United States Patent
Kajitani et al.

(10) Patent No.: US 11,909,824 B2
(45) Date of Patent: Feb. 20, 2024

(54) UPLOAD SYSTEM, UPLOAD METHOD, UPLOAD DEVICE, AND PROGRAM

(71) Applicant: NEC Corporation, Tokyo (JP)

(72) Inventors: Hiroshi Kajitani, Tokyo (JP); Toshinori Takemura, Tokyo (JP); Kentaro Nakahara, Tokyo (JP); Hannah Pokka, Tokyo (JP); Itsumi Haneda, Tokyo (JP); Akira Kamei, Tokyo (JP); Kenichiro Fukushi, Tokyo (JP); Chenhui Huang, Tokyo (JP); Zhenwei Wang, Tokyo (JP); Yuka Imai, Tokyo (JP); Koichi Morikawa, Tokyo (JP); Hiroshi Okuda, Tokyo (JP); Hiroaki Nakano, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 17/767,504

(22) PCT Filed: Oct. 21, 2019

(86) PCT No.: PCT/JP2019/041393
§ 371 (c)(1),
(2) Date: Apr. 8, 2022

(87) PCT Pub. No.: WO2021/079415
PCT Pub. Date: Apr. 29, 2021

(65) Prior Publication Data
US 2023/0188601 A1 Jun. 15, 2023

(51) Int. Cl.
*H04L 67/12* (2022.01)
*G01C 22/00* (2006.01)

(52) U.S. Cl.
CPC ............ *H04L 67/12* (2013.01); *G01C 22/006* (2013.01)

(58) Field of Classification Search
CPC .............................. H04L 67/12; G01C 22/006
See application file for complete search history.

(56) References Cited

U.S. PATENT DOCUMENTS

2017/0225033 A1 8/2017 Czaja

FOREIGN PATENT DOCUMENTS

| JP | 2014-090304 A | 5/2014 |
| JP | 2015-114189 A | 6/2015 |
| JP | 2016-087346 A | 5/2016 |
| JP | 2017-127522 A | 7/2017 |

OTHER PUBLICATIONS

Fukuda Yu, "Program, information processing device, information processing method, and information processing system"—JP 2016-087346 A (Year: 2016).*

(Continued)

*Primary Examiner* — Kim T Nguyen
(74) *Attorney, Agent, or Firm* — Sughrue Mion, PLLC (57) ABSTRACT

A mobile terminal detects a self-device being located at a predetermined location, and stops reception of sensing information from a module device that transmits the sensing information, if being located at the predetermined location is detected. A fixed device receives the sensing information from the module device, and transmits the sensing information to a cloud server.

7 Claims, 9 Drawing Sheets

(56) References Cited

OTHER PUBLICATIONS

Sotooka Y and Tonooka Y "Communication System Has Operation Condition Notification Unit That Notifies Operation Condition Of Mobile Router, When Specific Access Point Operation Management Unit Starts Operation As Access Point"—JP 2014-090304 A (Year: 2014).*

International Search Report for PCT Application No. PCT/JP2019/041393, dated Jan. 14, 2020.

JP Office Action for JP Application No. 2021-553191, dated Aug. 22, 2023 with English Translation.

* cited by examiner

UPLOAD SYSTEM, UPLOAD METHOD, UPLOAD DEVICE, AND PROGRAM

This application is a National Stage Entry of PCT/JP2019/041393 filed on Oct. 21, 2019, the contents of all of which are incorporated herein by reference, in their entirety.

TECHNICAL FIELD

The present invention relates to an upload system, an upload method, an upload device, and a program.

BACKGROUND ART

In order to measure the state of a human body, it has been proposed to attach to the human body a module device including a sensor that detects human body states. Patent Document 1 discloses a technique for converting an acceleration measurement signal into digital data by means of a mobile terminal and then forwarding it to a server device via a network (Paragraph 0058, and so forth).

CITATION LIST

Patent Literature
 [Patent Document 1] Japanese Unexamined Patent Application, First Publication No. 2017-127522

SUMMARY OF THE INVENTION

Problem to be Solved by the Invention

Incidentally, there are cases where a module device, such as the one mentioned above, including a sensor for measuring the state of a human body, wirelessly transmits sensing information to a remote device at a predetermined timing. For example, a user wears a module device and leaves home. A mobile terminal carried by the user receives sensing information sensed and transmitted by the module device and uploads/transmits it to a remote device such as a cloud server. In such a technique of uploading sensing information to a predetermined device, the success probability of that upload needs to be increased.

It is thus an example of an exemplary object of the present invention to provide an upload system, an upload method, an upload device, and a program for solving the problem mentioned above.

Means for Solving the Problem

A first exemplary aspect of the present exemplary embodiment is an upload system, wherein a first upload device includes; a location detection unit configured to detect a self-device being located at a predetermined location, and a reception stop unit configured to stop reception of sensing information from a module device that transmits the sensing information, if being located at the predetermined location is detected; and a second upload device includes a forwarding unit configured to receive the sensing information from the module device and forwards the sensing information to a cloud device.

A second exemplary aspect of the present exemplary embodiment is an upload method including: detecting, by a first upload device, a self-device being located at a predetermined location, and stopping, by the first upload device, reception of sensing information from a module device that transmits the sensing information, if being located at the predetermined location is detected; and receiving, by a second upload device, the sensing information from the module device and forwarding the sensing information to a cloud device.

A third exemplary aspect of the present exemplary embodiment is an upload device further included in an upload system including another upload device that includes a forwarding unit configured to receive sensing information from a module device and forward the sensing information to a cloud device, the upload device including: a location detection unit configured to detect a self-device being located at a predetermined location; and a reception stop unit configured to stop reception of the sensing information from the module device, if being located at the predetermined location is detected.

A fourth exemplary aspect of the present exemplary embodiment is an upload device further included in an upload system including another upload device that includes a location detection unit configured to detect the self-device being located at a predetermined location, and a reception stop unit configured to stop reception of sensing information from a module device, if being located at the predetermined location is detected, the upload device including a forwarding means for receiving the sensing information from the another module device and forwarding the sensing information to a cloud device.

A fifth exemplary aspect of the present exemplary embodiment is a program that causes a computer of an upload device further included in an upload system including another upload device that includes a forwarding unit configured to receive sensing information from a module device and forwards the sensing information to a cloud device, to function as: a location detection means for detecting the self-device being located at a predetermined location; and a reception stop means for stopping reception of the sensing information from the module device, if being located at the predetermined location is detected.

Advantageous Effects of Invention

According to the present invention, it is possible to increase the probability of a successful upload of sensing information to a predetermined device.

EXAMPLE EMBODIMENT

Hereunder, an upload device included in an upload system according to one exemplary embodiment of the present invention will be described.

Figure 1:
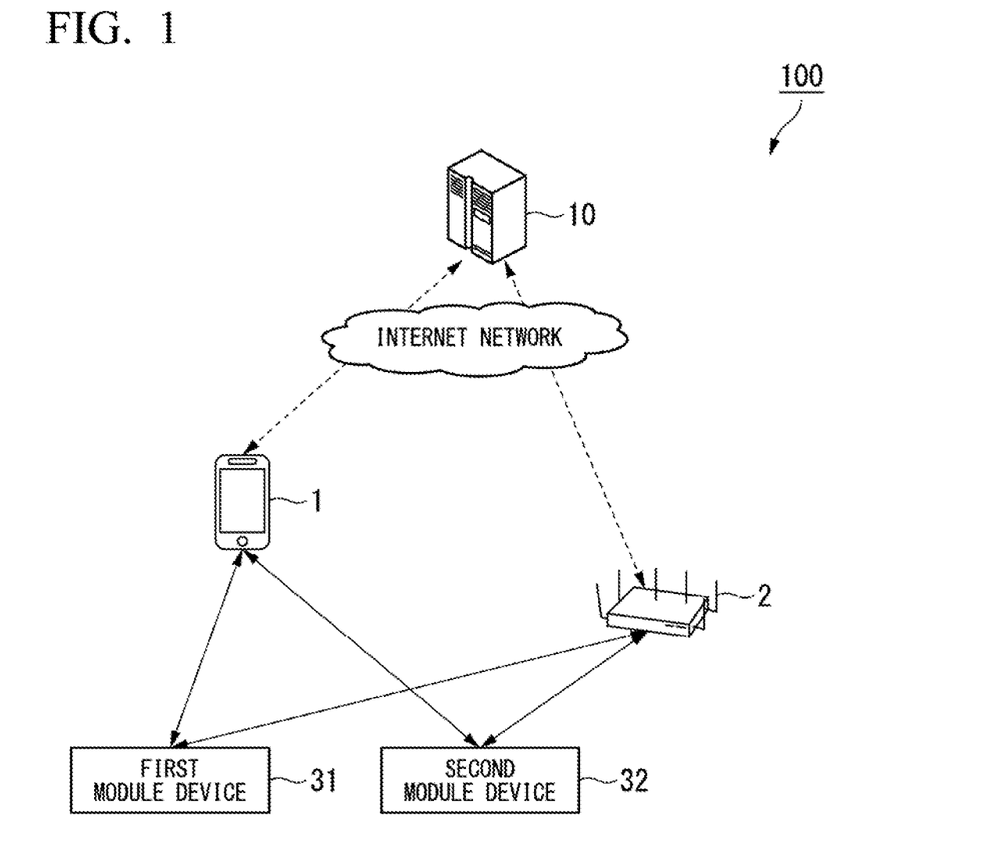
FIG. 1 is a diagram showing a schematic configuration of an upload system according to the present exemplary embodiment.

FIG. 1 is a diagram showing a schematic configuration of the upload system according to the same exemplary embodiment.

As shown in FIG. 1, an upload system 100 includes at least a mobile terminal 1 serving as an example of a first upload device, a fixed device 2 serving as an example of a second module device, and a first module device 31 and a second module device 32 attached respectively to left and right shoes.

The first module device 31 and the second module device 32 are collectively referred to simply as module devices 3. In the present exemplary embodiment, a description will be given of an example in which the upload system 100 includes two module devices 3, however, the upload system 100 may have only one module device 3.

The mobile terminal 1 is a computer to be carried and transported by a user. The mobile terminal 1 connects to and communicates with a cloud server 10 and other computers connected to the Internet network, primarily via a public wireless communication network. The mobile terminal 1 also wirelessly connects to and communicates with the first module device 31 and the second module device 32, and receives sensing information transmitted from those module devices 3. The mobile terminal 1 uploads received sensing information to the cloud server 10 at a first timing. Examples of the first timing include a case where the mobile terminal 1 is located outside the user's home.

The fixed device 2 is a computer installed in a fixed manner at the home or the like of the user possessing the mobile terminal 1. The fixed device 2 receives sensing information transmitted from the module device 3 and uploads it to the cloud server 10. Here, the mobile terminal 1 and the fixed device 2 are both devices that receive sensing information from the module device and forward it to the cloud server 10 to thereby upload the sensing information. Therefore, the mobile terminal 1 and the fixed device 2 are collectively referred to as upload devices.

Figure 2:
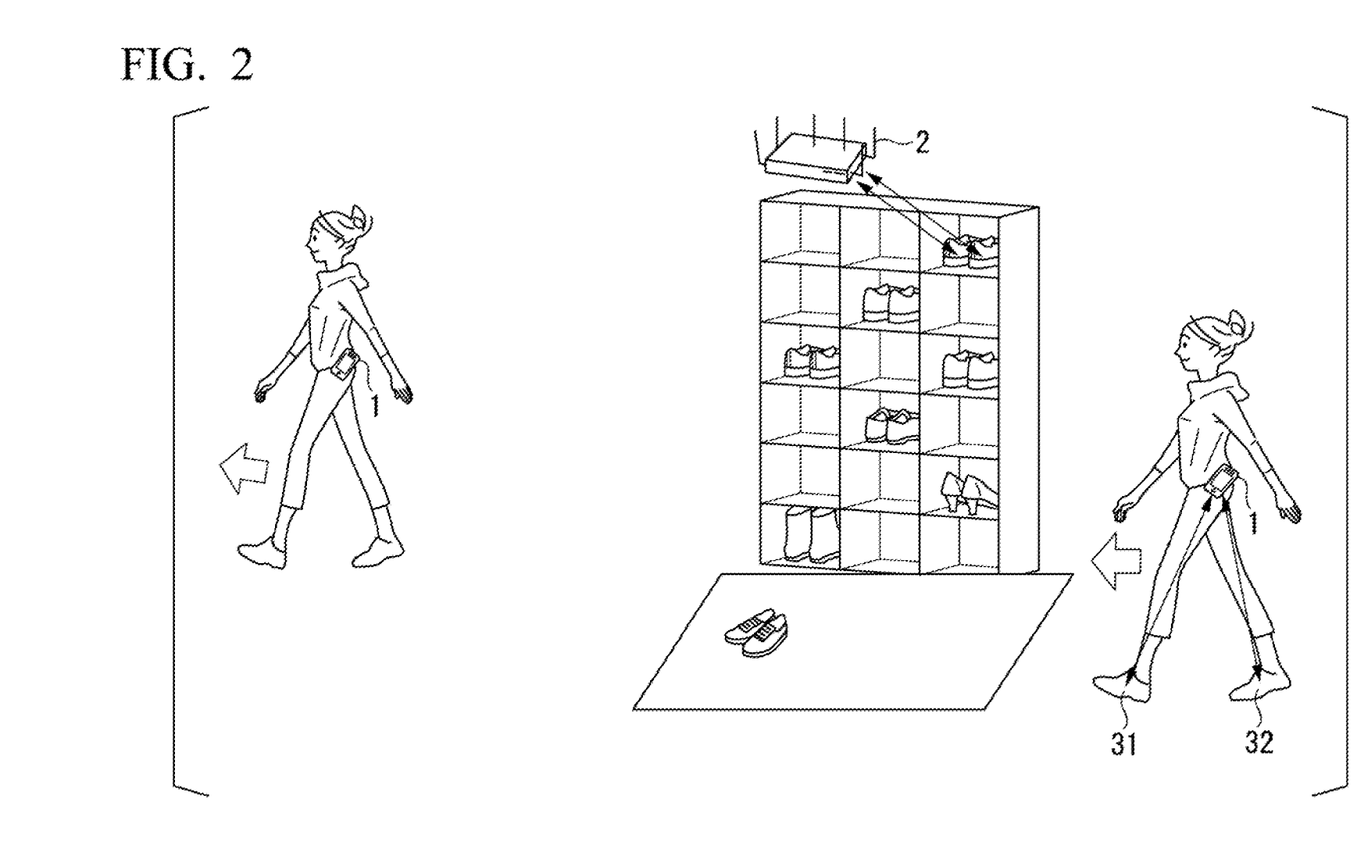
FIG. 2 is a diagram showing a process overview of a cloud system according to the present exemplary embodiment.

FIG. 2 is a diagram showing a process overview of a cloud system.

In the present exemplary embodiment, the module devices 3 are attached to shoes. For example, the first module device 31 is attached to the sole of a left shoe, and the second module device 32 is attached to the sole of a right shoe. The module devices 3 sense acceleration and angular velocity during walking. For example, the module devices 3 transmit to an upload device, sensing information including acceleration and angular velocity during walking.

More specifically, when the user is out carrying the mobile terminal 1 with them and communication with the mobile terminal 1 is possible, the module devices 3 use the mobile terminal 1 as an upload device to transmit sensing information to the mobile terminal 1. When sensing information is received, the mobile terminal 1 transmits (uploads) the sensing information to the cloud server 10. On the other hand, when the user carrying the mobile terminal 1 with them returns home, the module devices 3 use the fixed device 2 as an upload device instead of the mobile terminal 1, and transmit sensing information to the fixed device 2. When sensing information is received, the fixed device 2 transmits (uploads) the sensing information to the cloud server 10.

More specifically, when the user returns home, the mobile terminal 1 detects the self-terminal is located at home and stops receiving sensing information transmitted from the module devices 3. As a result, the module devices 3 become unable to communicate with the mobile terminal 1, and therefore attempt to establish a communication connection with another device. The fixed device 2 is always waiting to establish a communication connection with the module devices 3. Upon receiving a request for a communication connection from the module devices 3, the fixed device 2 automatically establishes a communication connection with the module devices 3. The module devices 3 transmit sensing information to the fixed device 2, where the fixed device 2, which is the destination of the communication connection newly established when the user has returned home, serves as an upload device. Upon receiving sensing information, the fixed device 2 transmits the sensing information to the cloud server 10.

As described above, in the upload system 100 according to the present exemplary embodiment, the mobile terminal 1, which is the first upload device, detects whether the self-terminal is located at a predetermined location, that is, the user's home in this case. Upon detecting the self-terminal as being at the predetermined location, the mobile terminal 1 stops receiving sensing information being transmitted from the module devices. The fixed device 2, which is the second upload device, then receives sensing information from the module devices 3 and transmits it to the cloud server 10. As a result, even in the case where the user takes off their shoes and enters a room upon returning home and the communication connection between the module devices 3 and the mobile terminal 1 can no longer be maintained because of the influence of the distance or obstacles between them, the fixed device 2 automatically establishes a communication connection with the module devices 3 because the locations of the shoes having the module devices 3 attached thereto are fixed in a shoe rack or in the vicinity of the entrance where the shoes are placed. As a result, the module devices 3 can upload sensing information to the cloud server 10 via the fixed device 2. Therefore, it is possible to increase the probability of a successful upload of sensing information to a predetermined device, that is, the cloud server 10 in this case.

Figure 3:
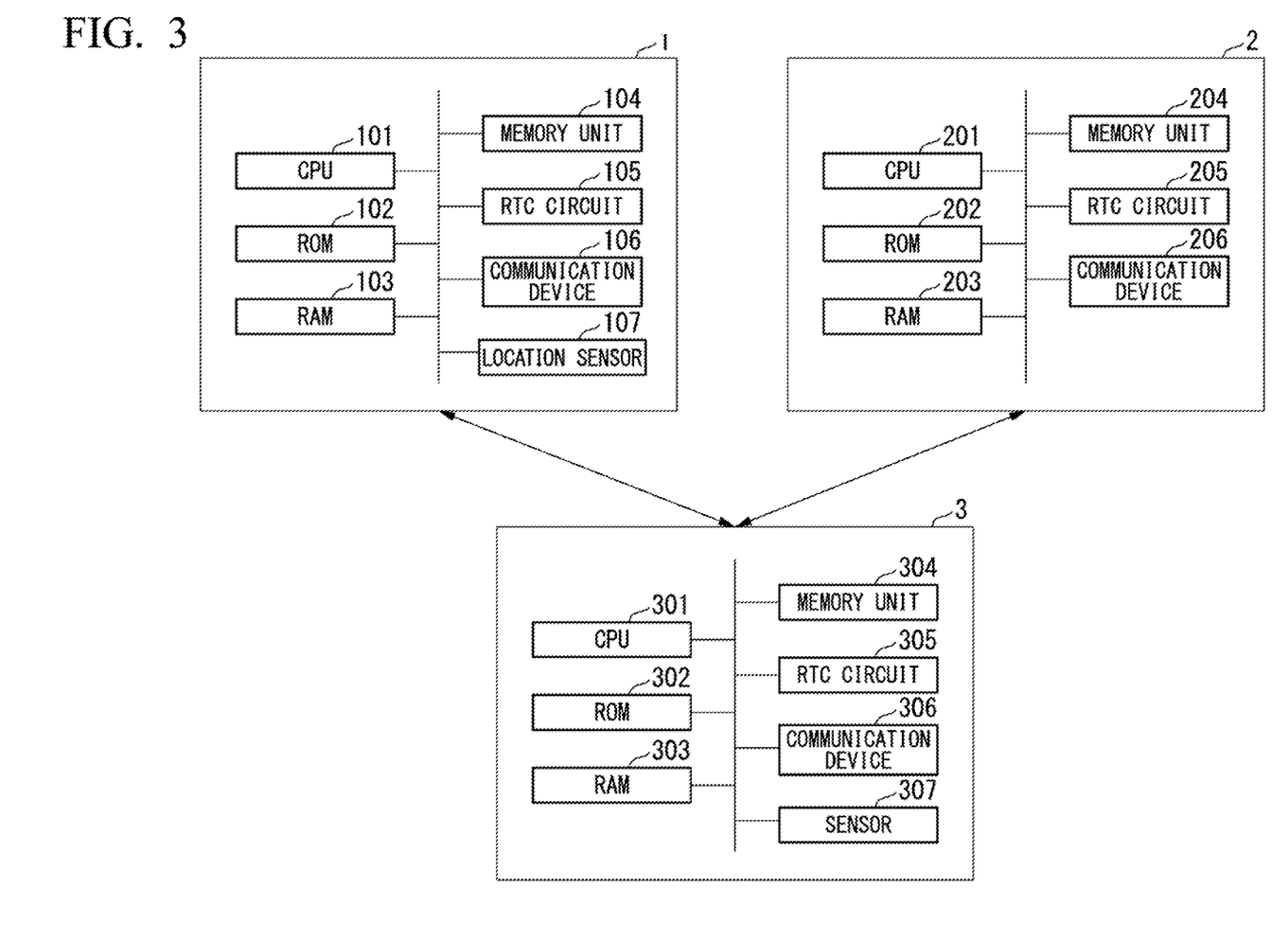
FIG. 3 is a hardware configuration diagram of a mobile terminal, a fixed device, and a module device according to the present exemplary embodiment.

FIG. 3 is a hardware configuration diagram of the mobile terminal, the fixed device, and the module device.

The mobile terminal 1 is a computer that includes hardware such as a CPU (Central Processing Unit) 101, a ROM (Read Only Memory) 102, a RAM (Random Access Memory) 103, a memory unit 104, an RTC (Real Time Clock) circuit 105, a communication device 106, and a location sensor 107. The location sensor 107 detects a location on the basis of signals received from artificial satellites such as a GNSS (Global Navigation Satellite System).

The fixed device 2 is also a computer that includes hardware such as a CPU 201, a ROM 202, a RAM 203, a memory unit 204, an RTC circuit 205, and a communication device 206.

Moreover, the module device 3 is a computer that includes hardware such as a CPU 301, a ROM 302, a RAM 303, a memory unit 304, an RTC circuit 305, a communication device 306, and a sensor 307. In the present exemplary embodiment, the module device 3 includes an inertial measurement unit (IMU) that senses acceleration and angular velocity on the basis of the movement of a foot when the user walks.

Figure 4:
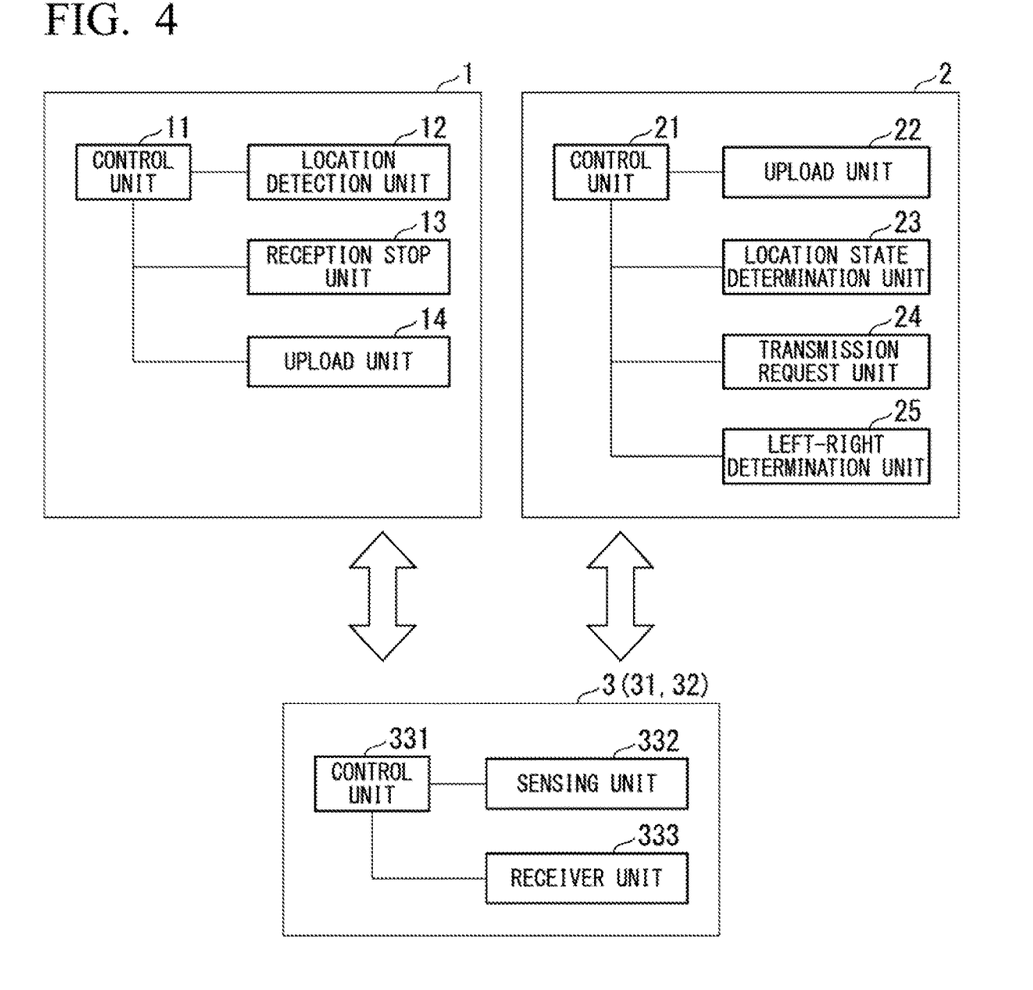
FIG. 4 is a function block diagram of the mobile terminal, the fixed device, and the module device according to the present exemplary embodiment.

FIG. 4 is a function block diagram of the mobile terminal, the fixed device, and the module device.

The mobile terminal 1 executes a first upload program that is preliminarily stored. As a result, the mobile terminal 1 exerts at least functions of a control unit 11, a location detection unit 12, a reception stop unit 13, and an upload unit 14.

The control unit 11 controls respective functions of the mobile terminal 1.

The location detection unit 12 detects location information at which the mobile terminal 1 is located, and detects whether the mobile terminal 1 is located at a predetermined location.

The reception stop unit 13 stops reception of sensing information from the module device 3 that transmits sensing information, if being located at the predetermined location is detected.

Upon receiving sensing information from the module device 3, the upload unit 14 forwards the sensing information to the cloud server 10.

The fixed device 2 executes a second upload program that is preliminarily stored. As a result, the fixed device 2 exerts at least functions of a control unit 21 and an upload unit 22. The fixed device 2 may further exert functions of a location state determination unit 23, a transmission request unit 24, and a left-right determination unit 25.

The control unit 21 controls respective functions of the fixed device 2.

Upon receiving sensing information from the module device 3, the upload unit 22 forwards the sensing information to the cloud server 10.

The location state determination unit 23 determines whether the placement location of the shoe having the module device 3 attached thereto, is a predetermined proximate location.

The transmission request unit 24 transmits a transmission request for sensing information to the module device 3.

The left-right determination unit 25 determines whether sensing information has been transmitted from the module device 3 attached to the left shoe or from that attached to the right shoe, on the basis of the reception strength of the sensing information received from the module device 3.

The module device 3 executes a sensing program that is preliminarily stored. As a result, the module device 3 exerts at least functions of a control unit 331, a sensing unit 332, and a transmission unit 333.

The control unit 331 controls respective functions of the module device 3.

The sensing unit 332 acquires, from the sensor 307 such as an IMU, sensing information such as acceleration and angular velocity on the basis of the movement of the left and right foot when the user walks.

The transmission unit 333 transmits sensing information to the mobile terminal 1 or the fixed device 2, which is an upload device.

Figure 5:
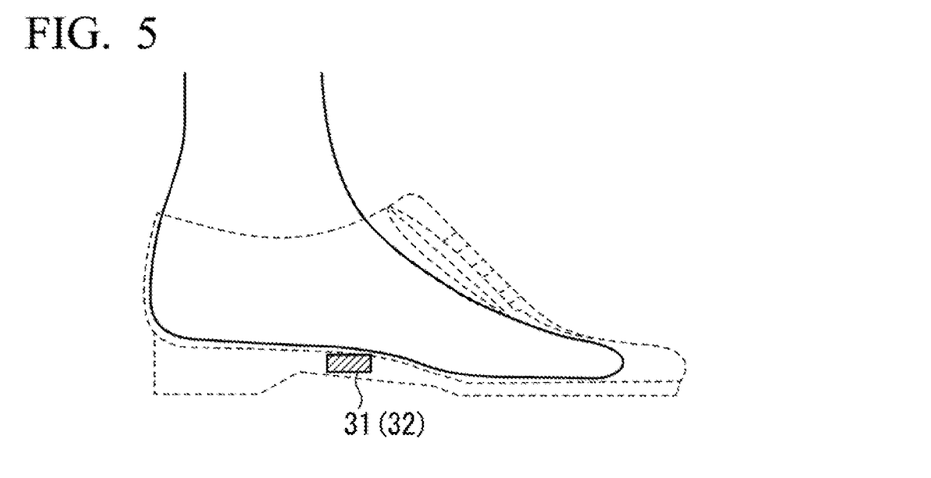
FIG. 5 is a diagram showing a brief overview of a sensor device included in a shoe sole according to the present exemplary embodiment.

FIG. 5 is a diagram showing a brief overview of a sensor device included in a shoe sole.

As shown in FIG. 5, the first module device 31 is attached to the sole of a left shoe and the second module device 32 is attached to the sole of a right shoe. The first module device 31 and the second module device 32 connect to and communicate with the mobile terminal 1 or the fixed device 2 by means of wireless communication.

First Exemplary Embodiment

Figure 6:
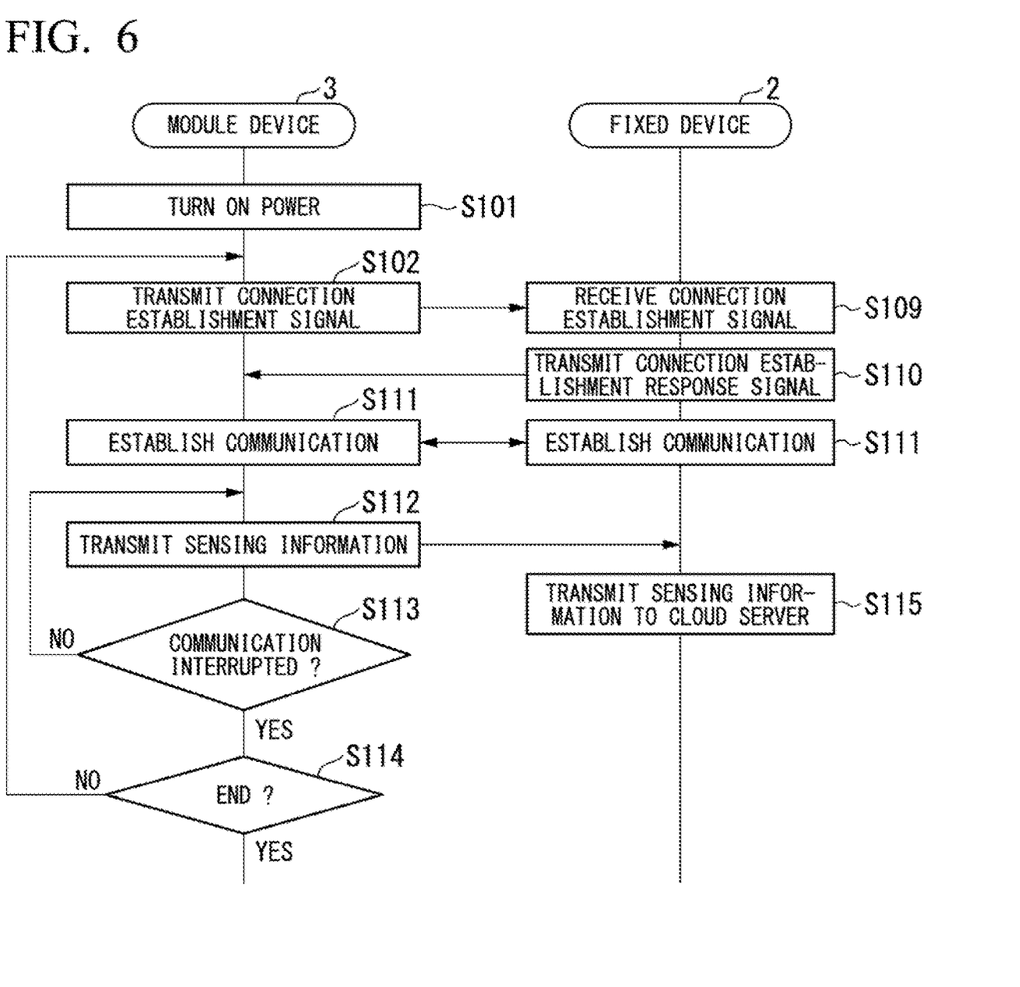
FIG. 6 is a first diagram showing a processing flow of respective devices in an upload system of the present exemplary embodiment.

FIG. 6 is a first diagram showing a processing flow of respective devices in an upload system of a first exemplary embodiment.

Figure 7:
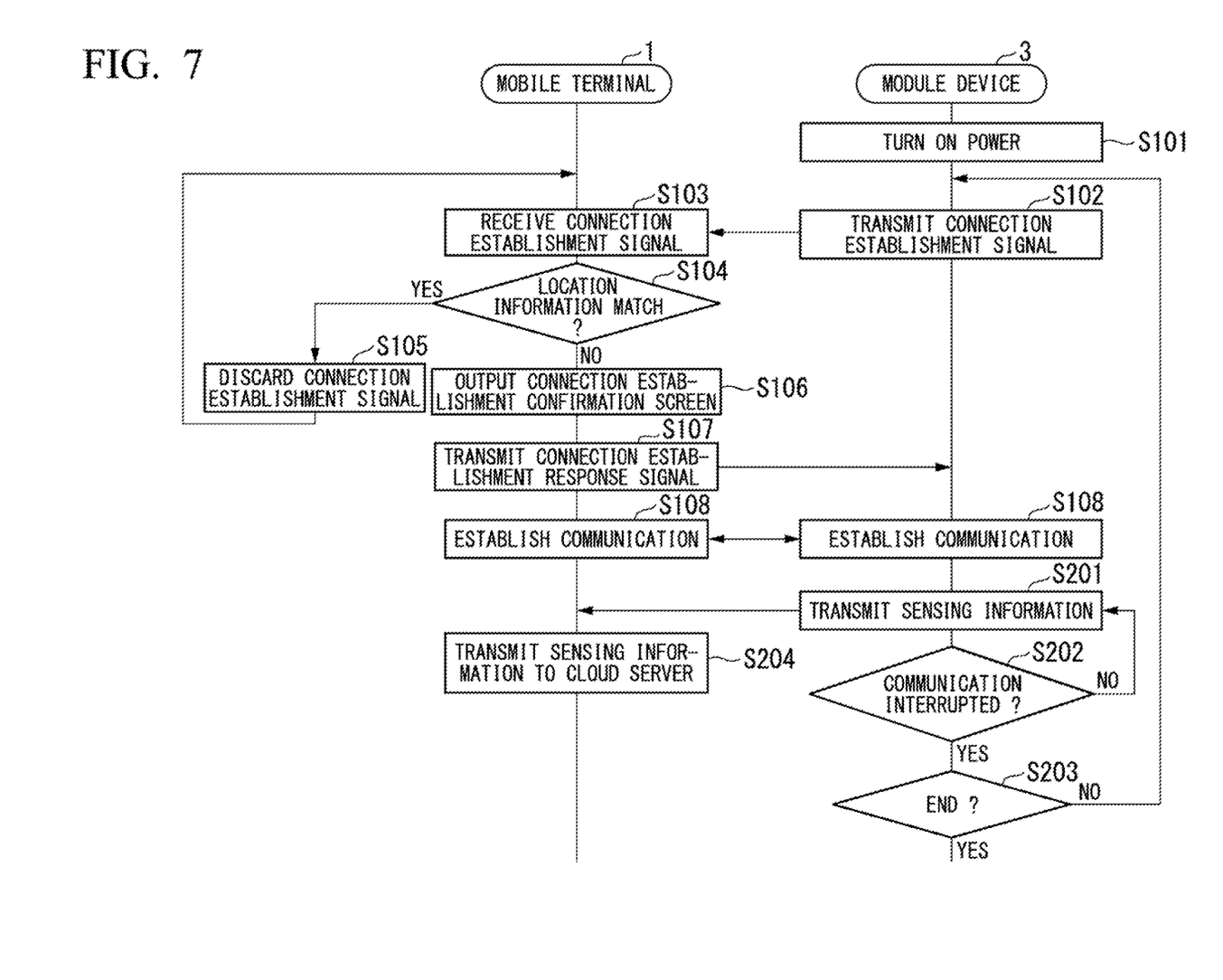
FIG. 7 is a second diagram showing a processing flow of respective devices in an upload system of a first exemplary embodiment.

FIG. 7 is a second diagram showing a processing flow of respective devices in the upload system of the first exemplary embodiment.

The user turns on the power of the first module device 31 and the second module device 32 (Step S101). As a result, the communication device 306 of the respective module devices 3, that is, the first module device 31 and the second module device 32, transmits a connection establishment signal (Step S102). The communication device 306 transmits a connection establishment signal to the mobile terminal 1 or the fixed device 2, using a wireless communication function such as BLE (Bluetooth Low Energy; registered trademark) or Wifi (registered trademark), for example. The module device 3 may be provided with a function to turn on the power automatically when sensing acceleration and so forth. As a result, the module device 3 can be activated without the user having to manually turn on the power of the module device 3.

The communication device 106 of the mobile terminal 1 receives the connection establishment signal (Step S103). The control unit 11 of the mobile terminal 1 detects the reception of the connection establishment signal. Upon detecting the reception of the connection establishment signal, the control unit 11 instructs the location detection unit 12 to perform location detection. The location detection unit 12 acquires location information of the mobile terminal 1 from the location sensor 107. The location detection unit 12 reads from the memory unit 104 the location information of the user's home that is stored preliminarily by the user's setting.

The location detection unit 12 compares the location information acquired from the location sensor 107 with the location information read from the memory unit 104, and determines whether they match with each other (Step S104). Location information matching with each other means that the distance between locations indicated by the location information is not greater than a predetermined distance, such as several meters. The distance between the location information being not greater than a predetermined distance means that the user is at home. If the locations indicated by location information match with each other, that is, if the user is determined as being at home since the location of the mobile terminal 1 and the location of the module device 3 are close to each other, the location detection unit 12 discards the connection establishment signal transmitted from the module device 3 (Step S105). As a result, the communication connection between the mobile terminal 1 and the module device 3 becomes unestablished.

If the location information acquired from the location sensor 107 and the location information read from the memory unit 104 do not match with each other, the location detection unit 12 notifies the control unit 11 of a location information mismatch. As a process to be performed in the case of a location information mismatch, the control unit 11 outputs a connection establishment confirmation screen to a display (Step S106). The connection establishment confirmation screen is a screen for accepting the user's determination as to whether to establish a communication connection between the module device 3 and the mobile terminal 1, and an OK button or the like is displayed thereon. The user presses the OK button in order to establish a communication connection between the module device 3 and the mobile terminal 1. As a result, the control unit 11 transmits a normal connection establishment response signal to the module device 3 (Step S107). Location information not matching with each other means that the user of the mobile terminal 1 carrying the mobile terminal 1 and wearing the shoes with the module devices 3 attached there to is out of home. The control unit 331 of the module device 3 receives the connection establishment response signal. The control unit 331 of the module device 3 then connects to and communicates with the mobile terminal 1, using a communication protocol for establishing a connection (Step S108). As a result, a communication connection between the mobile terminal 1 and the module device 3 is established.

On the other hand, the communication device 206 of the fixed device 2 also receives a connection establishment signal transmitted from the module device 3 (Step S109). The control unit 21 of the fixed device 2 detects the reception of the connection establishment signal. Upon detecting the connection establishment signal as having been received, the control unit 21 of the fixed device 2 transmits a normal connection establishment response signal to the module device 3 (Step S110). The control unit 331 of the module device 3 receives the connection establishment response signal. The control unit 331 of the module device 3 then connects to and communicates with the fixed device 2, using a communication protocol for establishing a connection. As a result, a communication connection between the fixed device 2 and the module device 3 is established.

The control unit 331 of the module device 3 controls the sensing unit 332 to acquire sensing information, in parallel with the process of communication connection with the fixed device 2. The sensing unit 332 acquires sensing information from the sensor 397. The sensing unit 332 outputs the sensing information to the transmission unit 333. The transmission unit 333 transmits the sensing information to the fixed device 2 (Step S112). The control unit 311 repeats the control of sensing information transmission. Also, the control unit 331 monitors communication connection and detects whether an interruption occurs in communication connection (Step S113). If the communication connection is interrupted, the control unit 331 determines whether to end the process (Step S114), and if the process is not to be ended, the process returns to Step S102 and the control unit 311 newly transmits a connection establishment signal. The fixed device 2 receives the sensing information transmitted in Step S112, and transmits the sensing information to the cloud server 10 (Step S115).

Through the processing described above, while the module device 3 is in the power ON state, the control unit 331 of the module device 3 performs the communication connection process so as to maintain the state where a communication connection can be established with either the mobile terminal 1 or the fixed device 2.

The user puts on shoes and leaves home. For example, as an example, the user leaves home for a jog, wearing the shoes with the module devices 3 attached thereto. The user leaves home, taking the mobile terminal 1 with them. As a result, the distance between the module device 3 and the fixed device 2 increases. When the distance between the module device 3 and the fixed device 2 exceeds a predetermined communicable distance, the module device 3 detects in the process of Step S113 that the communication connection with the fixed device 2 is interrupted. Then, if the process is not determined to be ended in Step S114, the control unit 331 of the module device 3 newly transmits a connection establishment signal through the process of Step S102.

The subsequent process is similar to that of Step S103 described above. That is to say, the communication device 106 of the mobile terminal 1 receives the connection establishment signal newly transmitted from the control unit 331 of the module device 3 (Step S103). The control unit 11 of the mobile terminal 1 detects the reception of the connection establishment signal. Upon detecting the reception of the connection establishment signal, the control unit 11 instructs the location detection unit 12 to perform location detection in a manner similar to that described above. The location detection unit 12 acquires the location information of the mobile terminal 1 from the location sensor 107. The location detection unit 12 reads from the memory unit 104 the location information of the user's home that is stored preliminarily by the user's setting.

The location detection unit 12 compares the location information acquired from the location sensor 107 with the location information read from the memory unit 104, and determines whether they match with each other (Step S104). If the user is out of home and is carrying the mobile terminal 1, the location detection unit 12 determines that the locations indicated by the location information do not match with each other. If the location information acquired from the location sensor 107 and the location information read from the memory unit 104 do not match with each other, the location detection unit 12 notifies the control unit 11 of a location information mismatch. As a process to be performed in the case of a location information mismatch, the control unit 11 outputs a connection establishment confirmation screen to a display (Step S106). The user presses the OK button in order to establish a communication connection between the module device 3 and the mobile terminal 1. As a result, the control unit 11 transmits a normal connection establishment response signal to the module device 3 (Step S107). When the user is carrying the mobile terminal 1, the mobile terminal 1 and the module device 3 are close to each other, so that a communication connection can be established.

The control unit 331 of the module device 3 receives the connection establishment response signal. The control unit 331 of the module device 3 connects to and communicates with the mobile terminal 1, using a communication protocol for establishing a connection (Step S108). As a result, a communication connection between the mobile terminal 1 and the module device 3 is established. After having established a communication connection, the control unit 331 of the module device 3 monitors the communication connection and detects whether an interruption occurs in the communication connection (Step S114). If the communication connection is interrupted, the control unit 331 returns to the process to Step S102 and newly transmits a connection establishment signal.

Through the processing described above, the module device 3 connects to and communicates with the fixed device 2 when the user is at home, and connects to and communicates with the mobile terminal 1 when the user is out of home wearing shoes with the module devices 3 attached thereto. Then, the module device 3 transmits sensing information to the upload device of either the mobile terminal 1 or the fixed device 2 that is connected thereto and communicating therewith.

When the module device 3 is connected to and communicating with the fixed device 2, the module device 3 transmits the sensing information stored in the memory unit of the self-device to the fixed device 2 (Step S115). For example, sensing information acquired while the user is out of home is stored in the memory unit, and whether the information recorded in the memory unit 304 is sensing information is determined when a communication connection is established with the fixed device 2. If the information recorded in the memory unit 304 is sensing information, the module device 3 transmits the sensing information to the fixed device 2. The communication device 206 of the fixed device 2 receives the sensing information. The upload unit 22 of the fixed device 2 uploads upload data including the sensing information, a user ID, and a module device ID to the cloud server 10. The sensing information may include the values of acceleration and angular velocity and the time at which the values are acquired.

As a result, when the user returns home, the fixed device 2 can upload to the cloud server 10 the uploaded data that includes the sensing information such as acceleration and angular velocity acquired by the module device 3 while the user is out of home, and the ID. The cloud server 10 records the ID of the user and the sensing information in a database or the like in association with each other. The cloud server 10 may perform a predetermined analytic process, using the sensing information of the user. For example, the cloud server 10 may analyze the walking state of the user on the basis of the sensing information of the user.

The module device 3 may be a device that senses other types of information other than acceleration and angular velocity. For example, the module device 3 may include a location sensor and transmit, as sensing information, a location to which the user has moved.

On the other hand, even when connected to and communicating with the mobile terminal 1, the control unit 331 of the module device 3 controls the sensing unit 332 to acquire sensing information, in parallel with the process of the communication connection. The sensing unit 332 acquires sensing information from the sensor 397. The sensing unit 332 outputs the sensing information to the transmission unit 333. The transmission unit 333 transmits the sensing information to the mobile terminal 1 (Step S201). The control unit 311 repeats the control of sensing information transmission. Also, the control unit 331 monitors communication connection and detects whether an interruption occurs in communication connection (Step S202). If the communication connection is interrupted, the control unit 331 determines whether to end the process (Step S203), and if the process is not to be ended, the process returns to Step S102 and the control unit 311 newly transmits a connection establishment signal. The upload unit 14 of the mobile terminal 1 receives the sensing information transmitted in Step S112, and transmits the sensing information to the cloud server 10 (Step S115).

As a result, when the user is out of home, the mobile terminal 1 can upload to the cloud server 10 the uploaded data that includes the sensing information such as acceleration and angular velocity acquired by the module device 3 while the user is out of home, and the ID. The cloud server 10 records the ID of the user, the ID of the module device, and the sensing information in a database or the like in association with each other.

While connected to and communicating with the mobile terminal 1, the module device 3 may continue to accumulate sensing information in the memory unit 304 of the self-device without transmitting it to the mobile terminal 1. As a result, it is possible to stop the uploading of sensing information to the cloud server 10 via the mobile terminal 1 that is performed outside home. Since the mobile terminal 1 receives sensing information from the module device 3 but does not upload it to the cloud server 10, use of a wireless communication line can be restricted.

Moreover, the module device 3 may store sensing information data in the memory unit 304 up to the full memory capacity of the memory unit 304, and when the memory volume of the memory unit 304 reaches the full memory capacity, sensing information may be transmitted to the mobile terminal 1. Upon receiving sensing information from the module device 3, the upload unit 14 of the mobile terminal 1 transmits upload data that includes the ID of the user, the ID of the module device, and the sensing information to the cloud server 10. Through such a process, the mobile terminal 1 uploads the sensing information that is transmitted from the module device 3 after the timing at which the memory volume of the module device 3 reaches the full memory capacity, so that use of a wireless communication line can be reduced.

Furthermore, while connected to and communicating with the mobile terminal 1, the module device 3 may receive a control signal transmitted by the mobile terminal 1 and, on the basis of the control signal, perform control such as changing information to be detected by the sensor 307. For example, in the case where the control signal is a control signal instructing to acquire acceleration, the module device 3 senses acceleration and stores the sensing information thereof or transmits the sensing information to the mobile terminal 1. Alternatively, in the case where the control signal received from the mobile terminal 1 is a control signal including information that instructs to change from acceleration to angular velocity, the module device 3 senses angular velocity and stores the sensing information thereof or transmits the sensing information to the mobile terminal 1.

Alternatively, while connected to and communicating with the mobile terminal 1, the module device 3 may periodically transmit sensing information to the mobile terminal 1, and the mobile terminal 1 may record the sensing information in the memory unit 104 of the self-terminal without uploading it to the cloud server 10. Then, if the location detection unit 12 determines that the mobile terminal 1 is located at home, the mobile terminal 1 may wirelessly transmit the sensing information recorded in the memory unit 104 to an Internet line access point connected to a wired communication network installed at home. As a result, use of a public wireless line can be restricted for the mobile terminal 1.

According to the above process, when the user returns home, the module device 3 and the fixed device 2 establish a communication connection and the module device 3 automatically transmits to the fixed device 2, the sensing information that was acquired by the module device 3 while the user was out of home wearing the shoes with the module devices 3 attached thereto and carrying the mobile terminal 1. The fixed device 2 then uploads the sensing information received from the module device 3 to the cloud server 10. As a result, when the user returns home, even if the communication connection between the mobile terminal 1 and the module device 3 is interrupted, it is possible to increase the probability of a successful upload of sensing information stored in the module device 3 to a predetermined device such as the cloud server 10.

Second Exemplary Embodiment

Figure 8:
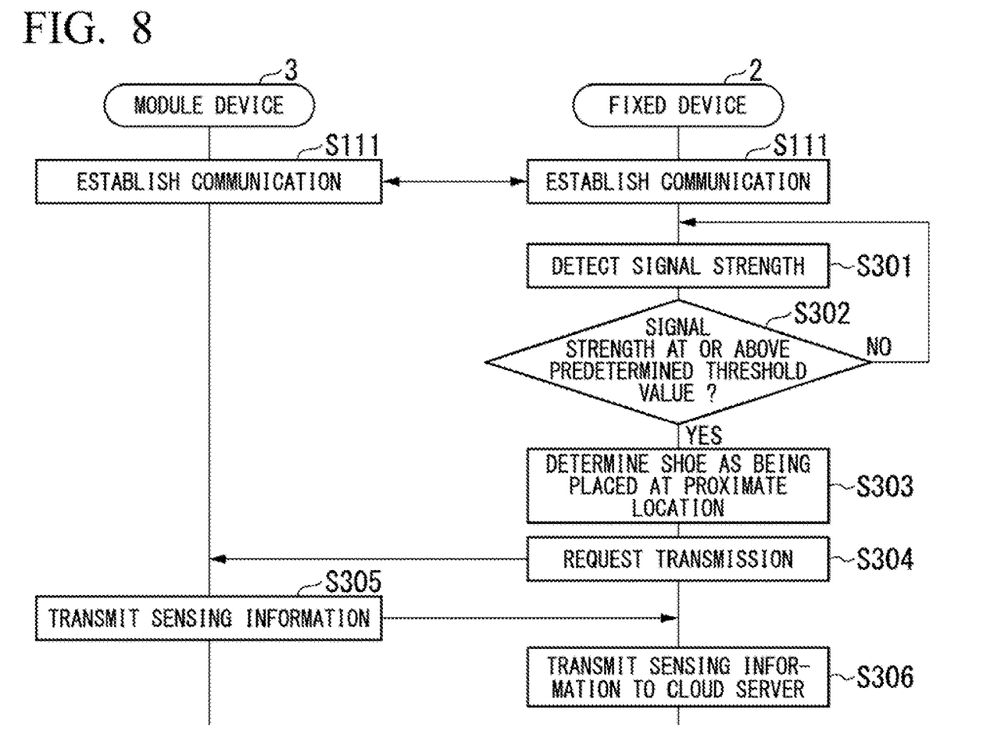
FIG. 8 is a diagram showing a processing flow of respective devices in an upload system of a second exemplary embodiment.

FIG. 8 is a diagram showing a processing flow of respective devices in an upload system of a second exemplary embodiment.

In the above process, the fixed device 2 may determine whether the placement location of the shoe to which the module device 3 is attached is a predetermined proximate location, receive the sensing information transmitted by the module device 3 attached to the shoe at the proximate location, and transmit it to the cloud server 10.

More specifically, the location state determination unit 23 of the fixed device 2 detects the signal strength of the communication connection with the module device 3 (Step S301). The location state determination unit 23 determines whether the signal strength of the communication connection with the module device 3 is at or above a predetermined threshold value (Step S302). If the signal strength of the communication connection with the module device 3 is at or above the predetermined threshold value, the location state determination unit 23 determines the shoe with the module device 3 attached thereto as being placed at the predetermined proximate location (Step S303).

For example, if the fixed device 2 is installed in a shoe box and the signal strength of the communication connection with the module device 3 is at or above the predetermined threshold value, the module device 3 (and the shoe with the module device 3 attached thereto) can be determined as being placed in the shoe box. In such a case, the possibility of the user putting again on the shoe with the module device 3 attached thereto and leaving home is low. Accordingly, by receiving sensing information from the module device 3 attached to the shoe placed in such a location, the module device 3 can upload the sensing information to the cloud server 10 at a time in a situation where the possibility of the user leaving home is low.

In the case where the location state determination unit 23 of the fixed device 2 determines the signal strength of the communication connection with the module device 3 as being below the predetermined threshold value, the control unit 21 may perform control so as to reject the reception of sensing information. As a result, when the next shoe is placed in the shoe box, the sensing information can be received and uploaded to the cloud server 10 all at once.

Here, if the location state determination unit 23 determines the signal strength of the communication connection with the module device 3 as being at or above the predetermined threshold value, the transmission request unit 24 transmits to the module device 3 a transmission request for sensing information (Step S304). As a result of this, the module device 3 transmits the sensing information to the fixed device 2 (Step S305).

For example, in the case where the control unit 331 of the module device 3 detects an interruption in the communication connection as the user returns home and the distance from the mobile terminal 1 increases, the control unit 331 establishes a communication connection with the fixed device 2 through the process of Step S111, and then, waits to receive a transmission request from the fixed device 2.

Then, in the process of Step S304, the transmission request unit 24 of the fixed device 2 acquires from the location state determination unit 23, the result of the location state determination unit 23 determining the signal strength of the communication connection with the module device 3 as being at or above the predetermined threshold value. If the signal strength of the communication connection is at or above the predetermined threshold value, the transmission request unit 24 transmits a transmission request for sensing information to the module device 3 in Step S304. The module device 3 receives the transmission request for sensing information. The transmission unit 333 of the module device 3 acquires sensing information from the memory unit 304 and transmits it to the fixed device 2 in the process of Step S305. The upload unit 22 of the fixed device 2 receives the sensing information, and transmits the sensing information to the cloud server 10 (Step S306).

According to such a process, in the state where the module device 3 is placed at a predetermined proximate location, the fixed device 2 can reliably and collectively receive sensing information accumulated in the module device 3 while out of home. Therefore, it is possible to increase the probability of a successful upload of sensing information to a predetermined device.

Third Exemplary Embodiment

Figure 9:
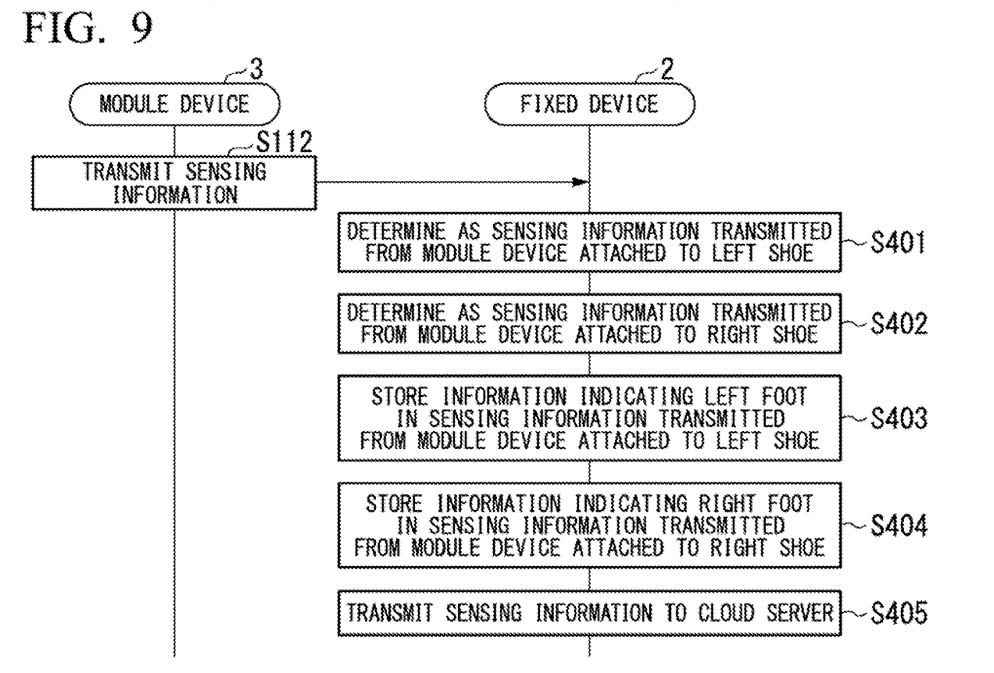
FIG. 9 is a diagram showing a processing flow of respective devices in an upload system of a third exemplary embodiment.

FIG. 9 is a diagram showing a processing flow of respective devices in an upload system of a third exemplary embodiment.

The fixed device 2 may include a left-right determination unit 25 that determines whether sensing information has been transmitted from the module device 3 attached to the left shoe or from that attached to the right shoe, on the basis of the reception strength of sensing information received from the module device 3. For example, the fixed device 2 memorizes whether the module device 3 of a high reception strength is a device attached to the left shoe or a device attached to the right shoe, on the basis of the installation location of the fixed device 2 in a shoe box, the location at which the shoes are placed, and how the shoes are placed in the shoe box. For example, in the case where, in the shoe box, the fixed device 2 is installed in a fixed manner at the left end thereof and the shoes are placed side by side with the toe-ends thereof facing the far end of the shoe box, the location of the module device 3 attached to the left shoe is closer to the fixed device 2 than the location of the module device 3 attached to the right shoe.

In such a case, on the basis of a reception strength with a high communication intensity, the left-right determination unit 25 of the fixed device 2 determines the sensing information of the reception strength as being sensing information transmitted from the module device 3 (first module device 31) attached to the left shoe (Step S401). Also, on the basis of a reception strength with a relatively low communication intensity, the left-right determination unit 25 determines the sensing information of the reception strength as being sensing information transmitted from the module device 3 (second module device 32) attached to the right shoe (Step S402).

If the received sensing information is determined as being sensing information transmitted from the module device 3 attached to the left shoe, the left-right determination unit 25 stores, in the sensing information, information indicating that the shoe is the left shoe (Step S403). If the received sensing information is determined as being sensing information transmitted from the module device 3 attached to the right shoe, the left-right determination unit 25 stores, in the sensing information, information indicating that the shoe is the right shoe (Step S404). The upload unit 22 uploads to the cloud server 10 the sensing information that stores the information indicating that the shoe is the left or right shoe (Step S405).

As a result, in a predetermined analysis that uses sensing information, the cloud server 10 can recognize whether it is the information of the left shoe or the information of the right shoe, and can perform a process according to the information.

Fourth Exemplary Embodiment

Figure 10:
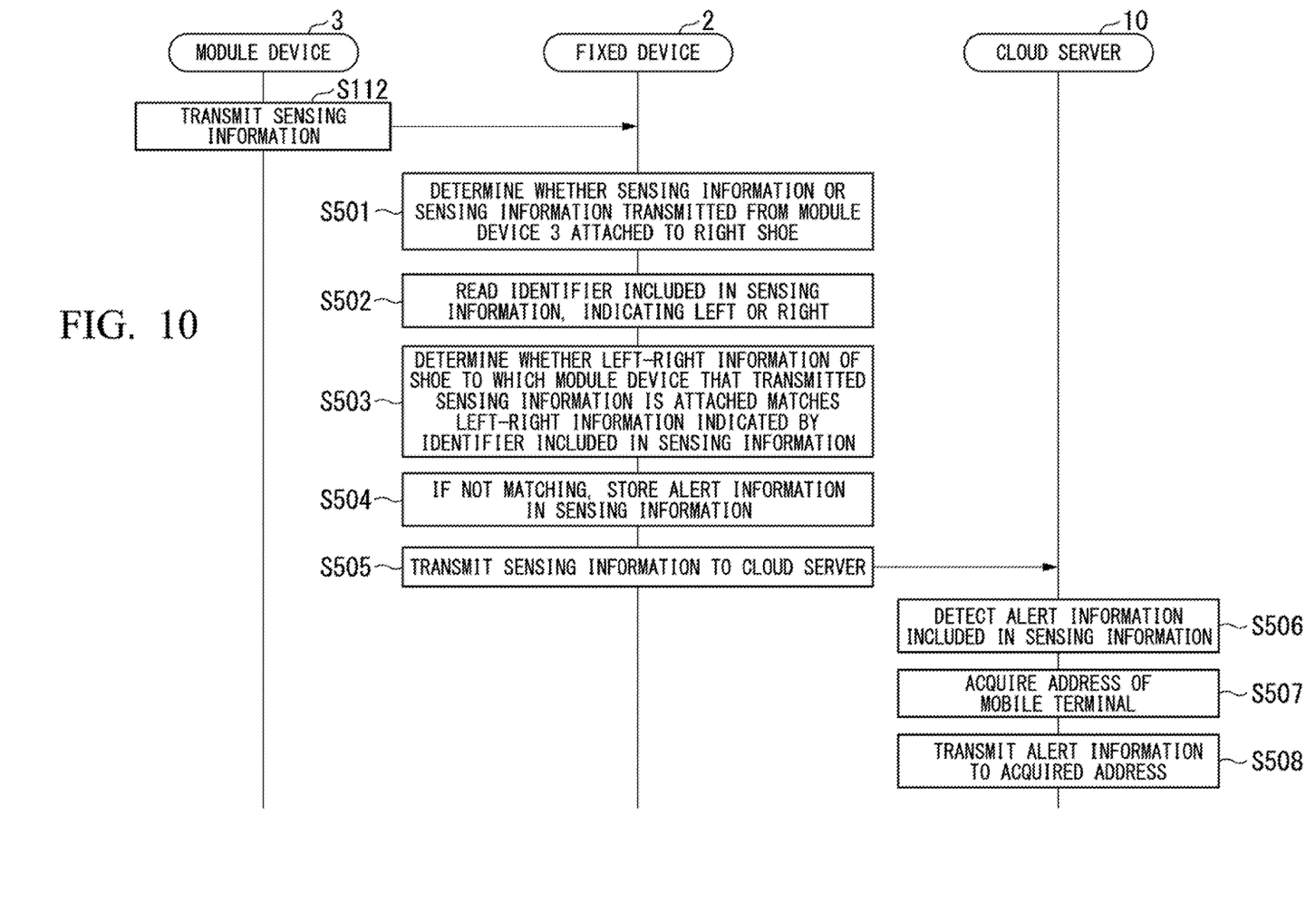
FIG. 10 is a diagram showing a processing flow of respective devices in an upload system of a fourth exemplary embodiment.

FIG. 10 is a diagram showing a processing flow of respective devices in an upload system of a fourth exemplary embodiment.

The left-right determination unit 25 of the fixed device 2 may determine whether the module devices 3 corresponding respectively to the left and right shoes are attached respectively to the left and right shoes, on the basis of information included in the sensing information received from the module devices 3 and the reception strength thereof. For example, the shapes of the module devices 3 differ from each other, depending on whether it is for the left or right shoe, and the shapes of insertion portions thereof for attaching the module devices 3 also differ from each other, depending on whether it is for the left or right shoe. Even under such a circumstance, there is a possibility that the user may still erroneously attach the module device 3 for the left shoe to the right shoe and the module device 3 for the right shoe to the left shoe, depending on the shape of the insertion portion or the flexibility of the material. The following describes an example of determining whether such a modular device 3 is appropriately attached to the left or right shoe.

As with the third exemplary embodiment, on the basis of a reception strength, the left-right determination unit 25 determines whether received sensing information is sensing information transmitted from the module device 3 attached to the left shoe or sensing information transmitted from the module device 3 attached to the right shoe (Step S501). Moreover, sensing information transmitted by the module device 3 includes an identifier of sensing information for the left shoe or the right shoe. This identifier is an identifier preliminarily recorded in the self-device when the module device 3 transmits sensing information, and the module device 3 transmits such sensing information to the fixed device 2. The left-right determination unit 25 of the fixed device 2 reads the identifier that is included in the sensing information and indicates left or right (Step S502).

The left-right determination unit 25 determines whether the left or right information of the shoe to which the module device 3 having transmitted sensing information is attached, which has been determined on the basis of the reception strength, matches with the left or right information indicated by the identifier included in the sensing information (Step S503). If the left or right information of the shoe to which the module device 3 having transmitted sensing information is attached does not match with the left or right information indicated by the identifier included in the sensing information, the left-right determination unit 25 stores alert information in the sensing information (Step S504). That is to say, for example, in the case where the module device 3 for the left shoe is attached to the right shoe, the left-right determination unit 25 determines that the left or right information of the shoe to which the module device 3 is attached that has transmitted the sensing information does not match with the left or right information indicated by the identifier included in the sensing information, and stores the alert information in the sensing information. The upload unit 22 then uploads the sensing information that stores the alert information to the cloud server 10 (Step S505).

The cloud server 10 receives the sensing information. The cloud server 10 detects the alert information included in the sensing information (Step S506). The cloud server 10 reads the user ID included in the sensing information, and acquires the address of the mobile terminal 1 stored preliminarily in association with the user ID (Step S507). The cloud server 10 transmits the alert information to the address (Step S508). This alert information is an alert indicating that the modular devices 3 are not attached to the corresponding left and right shoes appropriately and that the module device 3 for the left or right shoe is erroneously attached to the wrong shoe. The mobile terminal 1 receives the alert information and shows on the display a screen indicating that the module device 3 for the left or right shoe is erroneously attached to the wrong shoe. As a result, the user can confirm that the module device 3 for the left or right shoe is erroneously attached to the wrong shoe.

It should be noted that characteristics of acceleration and angular velocity sensed by the module device 3 differ, depending on whether it is for the left shoe or the right shoe. Therefore, it is necessary to always attach the module device 3 for the right shoe to the right shoe and the module device 3 for the left shoe to the left shoe. Moreover, when analyzing sensing information on the cloud server 10, the analysis needs to be performed upon correct recognition as to whether sensing information is of the left shoe or of the right shoe. According to the processing described above, it is possible to determine whether the modular devices 3 are appropriately attached to the left and right shoe.

Figure 11:
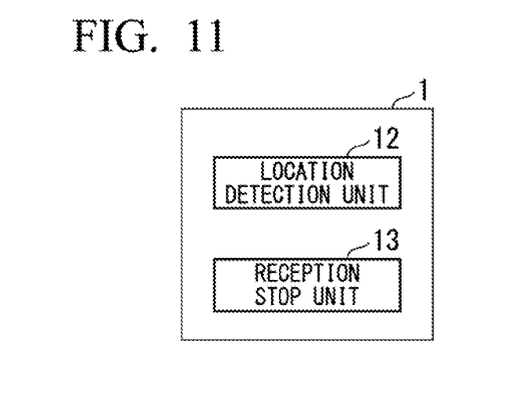
FIG. 11 is a diagram showing a minimum configuration of a mobile terminal according to the present exemplary embodiment.

FIG. 11 is a diagram showing a minimum configuration of a mobile terminal.

Figure 12:
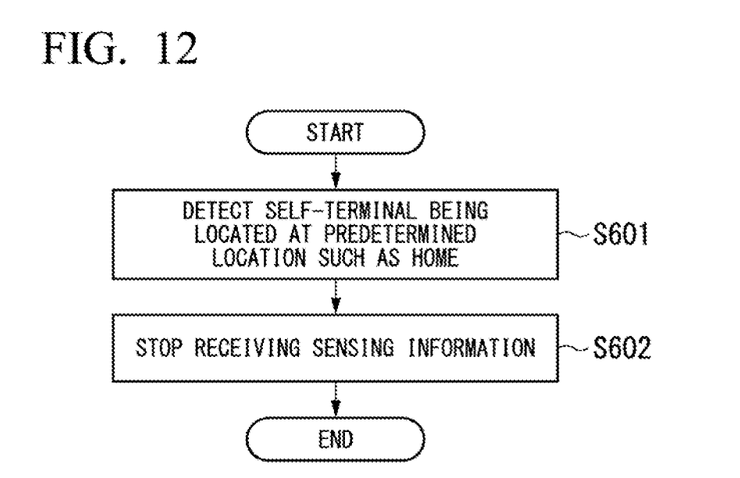
FIG. 12 is a diagram showing a processing flow by means of the mobile terminal of a minimum configuration according to the present exemplary embodiment.

FIG. 12 is a diagram showing a processing flow of the mobile terminal of the minimum configuration.

The mobile terminal 1, which is an example of the upload device, includes at least a location detection unit 12 and a reception stop unit 13.

The mobile terminal 1 is included in the upload system 100 including the fixed device 2, which is another upload device that includes the upload unit 22 for receiving sensing information from the module device 3 and transmitting it to the cloud server 10. In the mobile terminal 1, the location detection unit 12 detects the self-device being located at a predetermined location such as home (Step S601). Also, the mobile terminal 1 stops reception of sensing information from the module device 3 if the self-device is detected as being located at the predetermined location (Step S602).

Figure 13:
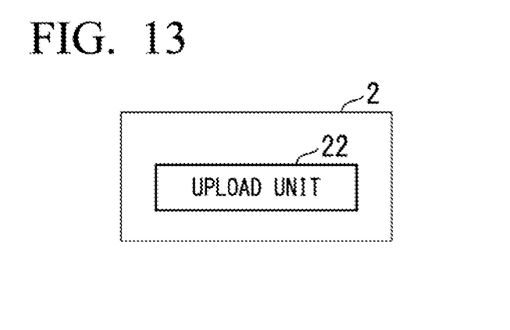
FIG. 13 is a diagram showing a minimum configuration of a fixed device according to the present exemplary embodiment.

FIG. 13 is a diagram showing a minimum configuration of a fixed device.

The mobile terminal 2, which is an example of the upload device, includes at least an upload unit 22. The upload unit 22 of the fixed device 2 receives sensing information transmitted from the module device 3 and uploads it to the cloud server 10.

Each device described above has a built-in computer system. The process of each processing described above is stored in a computer-readable recording medium in a form of a program, and the processing mentioned above is performed by a computer reading and executing the program. Here, the computer-readable recording medium refers to a magnetic disk, a magnetic optical disk, a CD-ROM, a DVD-ROM, a semiconductor memory, or the like. Moreover, the computer program may be distributed to a computer via a communication line, and the computer having received the distributed program may execute the program.

Also, this program may be a program for realizing some of the functions described above. Furthermore, the program may be a so-called difference file (a difference program) which can realize the functions described above in combination with a program already recorded in the computer system.

REFERENCE SYMBOLS

1 Mobile terminal (first upload device)
2 Fixed device (second upload device)
3 Module device
10 Cloud server
11, 21, 331 Control unit
12 Location detection unit
13 Reception stop unit
14, 22 Upload unit
23 Location state determination unit
24 Transmission request unit
25 Left-right determination unit
332 Sensing unit
333 Transmission unit

What is claimed is:

1. An upload system, comprising:
a first upload device; and
a second upload device, wherein
the first upload device includes:
at least one first memory configured to store first instructions; and
at least one first processor configured to execute the first instructions to:
detect the first upload device being located at a predetermined location, and
stop reception of sensing information from a module device that transmits the sensing information, if being located at the predetermined location is detected, and
a second upload device includes:
at least one second memory configured to store second instructions; and
at least one second processor configured to execute the second instructions to:
receive the sensing information from the module device and transmit the sensing information to a cloud device; and
determine whether the sensing information has been transmitted from the module device attached to a left shoe or from that attached to a right shoe, based on a reception strength of the sensing information received from the module device.

2. The upload system according to claim 1, wherein
the at least one second processor is configured to execute the second instructions to:
determine whether a placement location of a shoe having the module device attached thereto is a predetermined proximate location, and
receive the sensing information from the module device attached to the shoe at the predetermined proximate location and transmit the sensing information to the cloud device.

3. The upload system according to claim 2, wherein
the at least one second processor is configured to execute the second instructions to:
output a request for transmission of the sensing information to the module device if the placement location of the shoe is determined as the predetermined proximate location.

4. The upload system according to claim 1, wherein
the first upload device moves, and
the second upload device is fixed in a vicinity of a placement location of a shoe.

5. An upload system, comprising:
a first upload device; and
a second upload device, wherein
the first upload device includes:
at least one first memory configured to store first instructions; and
at least one first processor configured to execute the first instructions to:
detect the first upload device being located at a predetermined location, and
stop reception of sensing information from a module device that transmits the sensing information, if being located at the predetermined location is detected, and
the second upload device includes:
at least one second memory configured to store second instructions; and
at least one second processor configured to execute the second instructions to:
receive the sensing information from the module device and transmit the sensing information to a cloud device; and
determine whether module devices corresponding respectively to left and right shoes are attached respectively to the left and right shoes, based on information included in the sensing information received from the module device and a reception strength thereof.

6. An upload device further included in an upload system including another upload device that includes at least one first memory configured to store first instructions; and at least one first processor configured to execute the first instructions to detect the another upload device being located at a predetermined location, and stop reception of sensing information from a module device, if being located at the predetermined location is detected, the upload device comprising:
at least one second memory configured to store second instructions; and
at least one second processor configured to execute the second instructions to:
receive the sensing information from the module device and transmit the sensing information to a cloud device; and
determine whether the sensing information has been transmitted from the module device attached to a left shoe or from that attached to a right shoe, based on a reception strength of the sensing information received from the module device.

7. An upload device further included in an upload system including another upload device that includes at least one first memory configured to store first instructions; and at least one first processor configured to execute the first instructions to detect the another upload device being located at a predetermined location, and stop reception of sensing information from a module device, if being located at the predetermined location is detected, the upload device comprising:
at least one second memory configured to store second instructions; and
at least one second processor configured to execute the second instructions to:
receive the sensing information from the module device and transmit the sensing information to a cloud device; and determine whether module devices corresponding respectively to left and right shoes are attached respectively to the left and right shoes, based on information included in the sensing information received from the module device and a reception strength thereof.

* * * * *